United States Patent [19]

Krull et al.

[11] 4,203,435

[45] May 20, 1980

[54] WOUND DRESSING

[75] Inventors: Manfred Krull, Heiligkreutzsteinach; Holger Buchwald, Hemsbach; Wilhelm Kirsch, Birkenau, all of Fed. Rep. of Germany

[73] Assignee: Firma Carl Freudenberg, Weinheim, Fed. Rep. of Germany

[21] Appl. No.: 876,308

[22] Filed: Feb. 9, 1978

[30] Foreign Application Priority Data

Feb. 10, 1977 [DE] Fed. Rep. of Germany ... 7703897[U]

[51] Int. Cl.$^2$ ............................................. A61L 15/00
[52] U.S. Cl. ................................................... 128/156
[58] Field of Search ............................... 128/155–156, 128/284, 287, 290, 296

[56] References Cited

U.S. PATENT DOCUMENTS

| | | | |
|---|---|---|---|
| 3,043,301 | 7/1962 | Plantinga et al. | 128/296 |
| 3,067,747 | 12/1962 | Wolterding et al. | 128/296 |
| 3,089,488 | 5/1963 | Owens | 128/156 |
| 3,285,245 | 11/1966 | Eldredge et al. | 128/156 |
| 3,336,923 | 8/1967 | Devaud | 128/156 |
| 3,416,526 | 12/1968 | Yeremian | 128/156 |
| 3,441,021 | 4/1969 | Endres | 128/156 |
| 3,545,442 | 12/1970 | Wicker et al. | 128/156 |
| 3,858,585 | 1/1975 | Chatterjee | 128/296 |
| 3,888,257 | 6/1975 | Cook et al. | 128/296 |
| 3,971,379 | 7/1976 | Chatterjee | 128/290 |

*Primary Examiner*—Robert W. Michell
*Assistant Examiner*—C. F. Rosenbaum
*Attorney, Agent, or Firm*—Sprung, Felfe, Horn, Lynch & Kramer

[57] ABSTRACT

A wound dressing comprising at least five layers, the two outer layers comprising a permeable material non-adherent to a wound, below each outer layer there being arranged an absorbent layer each comprising cellulosic fibers, the absorbent layers being separated by a distribution layer comprising at least one of cellulose, carboxymethyl cellulose and a starch polymer. Advantageously the outer layers comprise a nonwoven fleece, a knit or woven fabric, or a perforated plastic sheet of at least one of polypropylene, polyethylene, polyesters, and polyamides, and the periphery of at least one of the outer layers carries a self-adhering adhesive inert to the skin. The entire structure is needled and, if fibrous, the outer layers are lightly thermally bonded so as to be fuzz-free.

1 Claim, No Drawings

WOUND DRESSING

This invention relates to a multi-layer wound dressing having an increased absorption efficiency and which does not stick to the wound. The wound dressing comprises a fibrous fleece.

Numerous wound dressings are compresses comprising fabrics or fleeces are known, using textile fibers or yarns of natural materials, for example cellulose or synthetic fibers. Natural substances have an extraordinarily good absorption but they quickly adhere to the wound. After drying up of the wound secretions, more or less serious difficulties are encountered when the bandage is removed. Healing of the wound is prevented by repeated opening of the wound. For this reason, in U.S. Pat. No. 3,285,245 it was already suggested to use as the upper layer for covering wounds synthetic textile fibers, perforated foils for example of polyesters, or polyolefin layers applied in powder form and sintered on. However, it was found that the wound secretion is taken up particularly in the vertical direction, and transported further. Thus, it may very quickly pass through to the upper side of the wound dressing.

An object of the invention is to develop a wound dressing which, on the one hand, has an increased absorption and, on the other hand, is not glued to the wound, and which prevents "break through" of the secretion to the surface of the bandage.

In accordance with the invention there is provided a multi-layer dressing comprising at least five layers, in which the two outer layers are of a permeable material not adherent to the wound and which, if desired, may have a polyolefin powder sintered thereon. Behind both sinter layers is an absorbent layer, each containing cellulose fibers and, optionally, a minor proportion of synthetic fibers. The absorbent layers are separated by a distribution layer comprising cellulose such as absorbent cotton, or carboxymethyl cellulose or starch polymers. As the material for the outer layers, there is used an appropriate non-woven fleece or fabric or a suitably perforated foil of a plastic inert to the skin.

By provision of the distribution layer in the middle of the dressing, a higher efficiency is achieved, the reason being that the secretion upon reaching this distribution layer is spread horizontally. The result is that not only the bandage material lying immediately above the wound is used for absorption. Only on saturation of a layer surface with secretion does secretion break through to the upper side. The distribution layer consists of tissue paper according to a preferred embodiment of the invention.

The novel wound dressing, through the distribution layer, additionally provides a higher security against infections from the outside because germs cannot penetrate the dry bandage material. It is known that a wet bandage material presents an increased infection risk. With the known dressings, for example according to U.S. Pat. No. 3,285,245, there is even an actual channel for fluids along which disease germs can get from the outside to the inside. Through the novel distribution layer the risk of infection has, however, been eliminated or substantially reduced.

Desirably at least both outer layers and the middle layer include a fleece material. The fleece material or materials preferably contain fibers of polypropylene, polyesters, polyethylene and/or polyamides. The outer layer contacting the skin can be provided at its periphery with a self-adhering glue inert to the skin. This embodiment is preferred in many cases, particularly with small wounds. However, it is also possible to fasten the dressing with adhesive tape or gauze.

Because of its smooth surface, the outer surface is less irritating to the skin than the usual gauzes. By structuring of the synthetic surface, an additional reduction in adherence to the skin and wound can be achieved, the absorbability remaining unchanged. Additionally, the air channels formed by the structuring further the healing.

By fixing a self-adhering glue at the periphery or on two edges of the dressing, an immediate and final placing over the wound is achieved so that slipping is prevented.

For the transport and sterilization of the dressing it is suitably covered with a release paper.

The gluing ribbon at the edge of the outer surfaces can be provided through the full thickness of the dressing. This avoids fiber fragments coming loose.

The invention is further described in the following illustrative examples:

EXAMPLE 1

On a fleece-forming apparatus equipped with a cross-layer there is prepared a fleece of 25 g/m$^2$ of 100% 6 dtex polypropylene fibers. Another nonwoven fleece weighing 100 g/m$^2$ and formed of 80 parts by weight of 1.4 dtex viscose staple fibers 40 mm long and 20 parts by weight of 3.3 dtex polyester staple fibers 60 mm long is positioned on this nonwoven material. The two gauzes are needled together lightly.

A pure cellulose pulp layer weighing 30 g/m$^2$ is placed on the needled structure, on the side containing the cellulose fibers, and a second needled composite is superposed so that the polypropylene fiber is on the outside. This 5-layered material construction is needled on both sides. The cohesion of the cellulose wadding lying in the middle is not destroyed by such needling to ensure its performance as a distributing layer.

The needled 5-layered material is brought to the softening temperature of the outer covering fiber in a belt drier, viz. 150° C. for the polypropylene. At the end of the drier there is a cooled set of rollers through which the material is passed. The synthetic fiber is bonded smoothly, a non-fuzzy surface resulting therefrom.

EXAMPLE 2

Onto a band of cellulose padding weighing 30 g/m$^2$ there is placed a nonwoven material comprising by weight 60 parts of cotton and 40 parts of viscose fibers. Onto this material there is placed a gauze of 25 g/m$^2$ of a sheath-core covering fiber (polypropylene-core; polyethylene-sheath). These three layers are needled together lightly without destroying the band of padding. Another nonwoven layer of cotton/viscose is placed onto the padding and another layer of sheath-core fiber is applied. This 5-layer material is needled lightly from both sides. The needled material then moves through a felt calender, the temperature of the Teflon-coated steel cylinder lying in the softening range of the polyethylene sheath of the sheath-core covering fiber. This process is conducted twice, once on each side.

EXAMPLE 3

On a card there is formed a web of undrawn polyester fibers weighing 25 g/m$^2$ over which there is laid a nonwoven fleece of 100% viscose staple fibers weighing 80

$g/m^2$. The structure is needled lightly in order to obtain a cohesion of the two layers. Over this is a layer of a material consisting of absorbent cotton (30 $g/m^2$) and powder of modified starch (5 $g/m^2$).

Another viscose layer is superimposed and then another undrawn polyester layer.

The entire structure is needled lightly from both sides without destroying the cohesion of the middle layer. The needled material is now passed through a calender with two steel rolls about each of which there runs a Teflon-coated fiberglass fabric belt. The rolls are heated to 220° C., and the undrawn polyester fibers are adhered to one another. The fiberglass belts extend beyond the rolls to a distance that the polyester fibers are cooled below softening temperature by ambient air before they leave the belts.

The weights of each layer can be varied widely depending upon the type of wound to be dressed, the selection of which dressing to select from an inventory of different weights and compositions resting with the doctor.

It will be appreciated that the instant specification and examples are set forth by way of illustration and not limitation, and that various modifications and changes may be made without departing from the spirit and scope of the present invention.

What is claimed is:

1. A wound dressing comprising at least five layers needled together into an integral structure, the two outer layers being permeable and non-adherent to a wound, the next two layers being absorbent layers substantially free of channels and comprising cellulosic fibers in the form of absorbent cotton, a nonwoven fleece or fabric, the absorbent layers being separated by a distribution layer comprising a powder of modified starch, the outer layers comprising polypropylene, polyethylene, polyester or polyamide in the form of a fibrous nonwoven fleece, knit or woven fabric or a perforated plastic sheet thermally bonded to form fuzz-free surfaces.

* * * * *